(12) United States Patent
Shepherd et al.

(10) Patent No.: US 12,011,516 B2
(45) Date of Patent: Jun. 18, 2024

(54) FOAM ACTUATORS

(71) Applicant: Cornell University, Ithaca, NY (US)

(72) Inventors: Robert F. Shepherd, Ithaca, NY (US); James K. Min, Brooklyn, NY (US); Benjamin C. Mac Murray, Ithaca, NY (US)

(73) Assignee: Cornell University, Ithaca, NY (US)

( * ) Notice: Subject to any disclaimer, the term of this patent is extended or adjusted under 35 U.S.C. 154(b) by 1192 days.

(21) Appl. No.: 16/310,638

(22) PCT Filed: Jun. 19, 2017

(86) PCT No.: PCT/US2017/038110
§ 371 (c)(1),
(2) Date: Dec. 17, 2018

(87) PCT Pub. No.: WO2018/005144
PCT Pub. Date: Jan. 4, 2018

(65) Prior Publication Data
US 2019/0321522 A1  Oct. 24, 2019

Related U.S. Application Data

(60) Provisional application No. 62/351,439, filed on Jun. 17, 2016, provisional application No. 62/351,448, filed on Jun. 17, 2016.

(51) Int. Cl.
*A61L 31/14* (2006.01)
*A61F 2/24* (2006.01)
(Continued)

(52) U.S. Cl.
CPC ............ *A61L 31/146* (2013.01); *A61L 31/06* (2013.01); *A61L 31/10* (2013.01); *A61M 60/191* (2021.01);
(Continued)

(58) Field of Classification Search
CPC .... C08J 2400/26; C08J 2300/26; C08J 9/365; C08J 7/04; C08J 7/042; A61L 31/146;
(Continued)

(56) References Cited

U.S. PATENT DOCUMENTS 3,675,377 A   7/1972  Suter
5,098,369 A   3/1992  Heilman et al.
(Continued)

FOREIGN PATENT DOCUMENTS

WO   1998050221      11/1998
WO   2007094433 A1   8/2007
(Continued)

OTHER PUBLICATIONS

Mac Murray, B.C., et al., Poroelastic Foams for Simple Fabrication of Complex Soft Robots, Advanced Materials, Nov. 4, 2015, vol. 27, Issue 41, pp. 6334-6340.
(Continued)

*Primary Examiner* — Maria V Ewald
*Assistant Examiner* — Daniel P Dillon
(74) *Attorney, Agent, or Firm* — Barnes & Thornburg LLP

(57) ABSTRACT

Foam-based pneumatic actuators can be formed in a state of mechanical compression prior to actuation. An actuator includes an elastomeric foam; a coating disposed on the elastomeric foam; and an elastomer seal disposed on the coating. The coating constrains the elastomeric foam and can be configured to break or fracture when the elastomeric foam inflates. The elastomer seal can be configured to be impermeable to the actuating fluid. Such a foam actuator can be used in a cardiac compression device. These foam actuators possess increased actuation deformation and an
(Continued)

actuation exerted force for a given inflation pressure. A large deformation can be provided from materials having low ultimate strains.

32 Claims, 8 Drawing Sheets

(51) Int. Cl.
| | | |
|---|---|---|
| *A61L 31/06* | (2006.01) | |
| *A61L 31/10* | (2006.01) | |
| *A61M 60/191* | (2021.01) | |
| *A61M 60/289* | (2021.01) | |
| *A61M 60/43* | (2021.01) | |
| *A61M 60/468* | (2021.01) | |
| *A61M 60/839* | (2021.01) | |
| *C08J 7/04* | (2020.01) | |
| *F16F 5/00* | (2006.01) | |

(52) U.S. Cl.
CPC .......... *A61M 60/289* (2021.01); *A61M 60/43* (2021.01); *A61M 60/468* (2021.01); *A61M 60/839* (2021.01); *C08J 7/042* (2013.01); *F16F 5/00* (2013.01); *A61F 2/2481* (2013.01); *A61L 2420/02* (2013.01); *C08J 2400/26* (2013.01)

(58) Field of Classification Search
CPC ...... A61L 31/06; A61L 31/10; A61L 2420/02; A61M 60/268; A61M 60/43; A61M 60/148; A61M 60/468; A61M 60/839; F16F 5/00; A61F 2/2481
See application file for complete search history.

(56) References Cited

U.S. PATENT DOCUMENTS

| | | | |
|---|---|---|---|
| 5,196,242 | A | 5/1993 | Vicino |
| 5,250,167 | A | 10/1993 | Adolf et al. |
| 6,309,341 | B1 | 10/2001 | Denker |
| 6,384,296 | B1 | 5/2002 | Roe et al. |
| 6,432,039 | B1 | 8/2002 | Wardle |
| 6,602,182 | B1 | 8/2003 | Milbocker |
| 10,058,647 | B2 | 8/2018 | Roche et al. |
| 11,097,090 | B2 | 8/2021 | Vasilyev et al. |
| 2002/0007216 | A1 | 1/2002 | Melvin |
| 2004/0167375 | A1 | 8/2004 | Couvillon, Jr. |
| 2004/0225177 | A1 | 11/2004 | Coleman et al. |
| 2006/0142634 | A1 | 6/2006 | Anstadt et al. |
| 2008/0015540 | A1* | 1/2008 | Muni ................. A61B 17/3421 604/502 |
| 2008/0132749 | A1 | 6/2008 | Hegde et al. |
| 2009/0301292 | A1* | 12/2009 | Kothera ................. B21D 39/04 29/237 |
| 2011/0004137 | A1 | 1/2011 | Cornacchio et al. |
| 2013/0175898 | A1 | 7/2013 | Brokken et al. |
| 2014/0069212 | A1 | 3/2014 | Fishel et al. |
| 2015/0112130 | A1 | 4/2015 | Shepherd et al. |
| 2016/0017899 | A1* | 1/2016 | Yang ......................... A61F 2/08 92/261 |
| 2016/0199167 | A1* | 7/2016 | Cotner ................. A61F 2/0036 600/30 |
| 2017/0029592 | A1 | 2/2017 | Shepherd et al. |

FOREIGN PATENT DOCUMENTS

| | | | |
|---|---|---|---|
| WO | 2009096967 | | 8/2009 |
| WO | 2014078458 A2 | | 5/2014 |
| WO | 2015023803 | | 2/2015 |
| WO | 2015157560 | | 10/2015 |
| WO | 2015157560 A1 | | 10/2015 |
| WO | WO-2015157560 A1 * | 10/2015 | ............... C08J 9/08 |
| WO | 2016012689 A2 | | 1/2016 |
| WO | 2017032790 A1 | | 3/2017 |

OTHER PUBLICATIONS

Mac Murray, B.C., et al., Compliant, buckled-foam pneumatic actuators and application in a patient-specific cardiac assist device, Apr. 17-21, 2017, 2017 MRS (Materials Research Society) Spring Meeting, 2 pages.

Shepherd, R.,F., et al., Soft robotics: Poroelastic foams for simple fabrication of complex soft robots, Advanced Materials, Nov. 2, 2015, vol. 27, No. 41, p. 6334.

Roche, E.T., et al., Soft robotic sleeve supports heart function, Science Translational Medicine, Jan. 18, 2017, vol. 9, No. 373, pp. 1-11.

Roche, E.T., et al., Draft: Design and Fabrication of a Soft Robotic Direct Cardiac Compression Device, Proceedings of the ASME 2015 International Design Engineering Technical Conferences & Computers and Information in Engineering Conference, Aug. 2-5, 2015, pp. 1-11.

Kavarana, M.N., et al., Circulatory support with a direct cardiac compression device: A less invasive approach with the AbioBooster device, The Journal of Thoracic and Cardiovascular Surgery, Oct. 2001, vol. 122, No. 4, pp. 786-787.

Kavarana, M.N., et al., Pediatric Mechanical Support with an External Cardiac Compression Device, J Cardiovasc Dis Diagn., Sep. 11, 2013, vol. 1, No. 2, pp. 1-15.

* cited by examiner

FOAM ACTUATORS

CROSS-REFERENCE TO RELATED APPLICATIONS

This application claims priority to the provisional patent application filed Jun. 17, 2016 and assigned U.S. App. No. 62/351,439, and to the provisional patent application filed Jun. 17, 2016 and assigned 62/351,448, the disclosures of which are hereby incorporated by reference.

STATEMENT REGARDING FEDERALLY-SPONSORED RESEARCH OR DEVELOPMENT

This invention was made with government support under contract no. FA9550-15-1-0160 awarded by the Air Force Office of Scientific Research. The government has certain rights in the invention.

FIELD OF THE DISCLOSURE

This disclosure relates to foam actuators.

BACKGROUND OF THE DISCLOSURE

The field of soft robotics uses compliant structures to reduce machine complexity and approach the mechanical and sensing capabilities of biology. Soft (i.e., compliant and extensible) materials and structures have enabled machines capable of elaborate locomotion as well as analogs for caterpillars, fish, jellyfish, and octopus tentacles. These compliant machines often perform favorably when compared with conventional, rigid machines as they reduce control complexity, enable natural motion through continuous deformation, and interact gently with fragile objects.

Fluidic elastomer actuators (FEAs) are a class of compliant machines capable of producing large deformations via pressurization of internal bladders. They operate similar to McKibben artificial muscles, though often require lower pneumatic pressures. When internally pressurized, FEAs (typically composed of low elastic modulus silicone rubber) can bend, extend, or twist based on the specific patterning of inextensible fibers within the structure. During inflation, the inextensible fibers create a strain gradient resulting in the programmed motion. Although these machines exhibit complex motions with relatively few actuators, their fabrication has been largely limited to prismatic structures, which require complex assemblies to approximate the shapes and motions of biological models. Furthermore, these actuators require internal, connecting air chambers that often necessitate complex, costly, and time-consuming mold fabrication. Foam-wax composites have been used to create soft, smart 3D structures that transcend prismatic designs, however these porous materials have not yet been used for fluidic actuation.

Some devices with actuators have medical applications. For example, the "Criscione device" and the "Anstadt Cup" are cardiac compression devices, but do not incorporate elastomer foam. Additionally, neither has been approved for clinical use.

Therefore, what is needed is an improved actuator.

BRIEF SUMMARY OF THE DISCLOSURE

In a first embodiment, an actuator is provided. The actuator comprises an elastomeric foam, a coating disposed on the elastomeric foam, and an elastomer seal disposed on the coating. The elastomeric foam is a pre-compressed porous material. The coating is configured to constrain the elastomeric foam and is configured to break or fracture when the elastomeric foam inflates. The elastomer seal is configured to be impermeable to actuating fluid.

In a second embodiment, a method is provided. A coating is applied to an elastomeric foam. The elastomeric foam is a pre-compressed porous material. The coating is configured to constrain the elastomeric foam and is configured to break or fracture when the elastomeric foam inflates. The elastomeric foam is compressed after applying the coating. An elastomer seal is applied to the coating. The elastomer seal is configured to be impermeable to actuating fluid.

In a third embodiment, a cardiac compression device is provided. The cardiac compression device includes a foam actuator that has a contour configured to fit over at least part of an exterior contour of a heart. The foam actuator includes an elastomeric foam, a coating disposed on the elastomeric foam, and an elastomer seal disposed on the coating. The elastomeric foam is a pre-compressed porous material. The coating is configured to constrain the elastomeric foam and is configured to break or fracture when the elastomeric foam inflates. The elastomer seal is configured to be impermeable to actuating fluid.

Statement 1. An actuator comprises an elastomeric foam, a coating disposed on the elastomeric foam, and an elastomer seal disposed on the coating. The elastomeric foam is a pre-compressed porous material. The coating is configured to constrain the elastomeric foam and is configured to break or fracture when the elastomeric foam inflates. The elastomer seal is configured to be impermeable to actuating fluid.

Statement 2. The actuator of Statement 1, wherein the porous material is one of polyurethane, silicone, styrene, latex rubber, butadiene rubber, or copolymers thereof.

Statement 3. The actuator of Statement 1 or Statement 2, wherein the coating is one of non-porous polyurethane, silicone, styrene, latex rubber, butadiene rubber, a thermoplastic, a thermoset polymer, or a resin.

Statement 4. The actuator of one of Statements 1-3, wherein the elastomer seal is one of non-porous polyurethane, silicone, styrene, latex rubber, butadiene rubber, a thermoplastic, a thermoset polymer, or a resin.

Statement 5. The actuator of one of Statements 1-4, wherein the coating has a thickness from 0.5 mm to 2.0 mm.

Statement 6. The actuator of one of Statements 1-5, wherein the elastomer seal has a thickness of greater than or equal to 1 mm.

Statement 7. The actuator of Statement 6, wherein the elastomer seal has a thickness of greater than or equal to 2 mm.

Statement 8 The actuator of one of Statements 1-7, wherein the elastomer seal has a thickness at least twice a thickness of the coating.

Statement 9. The actuator of one of Statements 1-8, wherein the elastomer seal is from 1 cm to 2 cm thick, and wherein the thickness of the elastomer seal is 100× thicker than a thickness of the coating.

Statement 10. The actuator of one of Statements 1-9, further comprising inextensible mesh layers or fibers disposed on the elastomer seal, wherein the inextensible mesh layers or fibers are configured to direct inflated motion.

Statement 11. The actuator of one of Statements 1-10, wherein the coating is configured to break and cause preferential expansion of the elastomer in one or more directions and/or cause asymmetric expansion of the elastomer.

Statement 12. A method comprising: applying a coating to an elastomeric foam; compressing the elastomeric foam after applying the coating; and applying an elastomer seal to the coating. The elastomeric foam is a pre-compressed porous material. The coating is configured to constrain the elastomeric foam and is configured to break or fracture when the elastomeric foam inflates. The elastomer seal is configured to be impermeable to actuating fluid.

Statement 13. The method of Statement 12, wherein the method is configured to form the foam in a state of mechanical compression prior to actuation.

Statement 14. The method of Statement 12 or Statement 13, wherein the elastomeric foam is one of polyurethane, silicone, styrene, latex rubber, butadiene rubber, copolymers thereof, or another porous material.

Statement 15. The method of one of Statements 12-14, wherein the coating is one of non-porous polyurethane, silicone, styrene, latex rubber, butadiene rubber, a thermoplastic, a thermoset polymer, or a resin.

Statement 16. The method of one of Statements 12-15, wherein the elastomer seal is one of non-porous polyurethane, silicone, styrene, latex rubber, butadiene rubber, a thermoplastic, a thermoset polymer, or a resin.

Statement 17. The method of one of Statements 12-16, wherein the coating has a thickness from 0.5 mm to 2.0 mm.

Statement 18. The method of one of Statements 12-17, wherein the elastomer seal has a thickness of greater than or equal to 1 mm.

Statement 19. The method of Statement 18, wherein the elastomer seal has a thickness of greater than or equal to 2 mm.

Statement 20. The method of one of Statements 12-19, wherein the elastomer seal has a thickness 2× or more than 2× a thickness of the coating.

Statement 21. The method of one of Statements 12-20, wherein the elastomer seal is from 1 cm to 2 cm thick, and wherein the thickness of the elastomer seal is 100× thicker than a thickness of the coating.

Statement 22. The method of one of Statements 12-21, further comprising applying inextensible mesh layers or fibers to the elastomer seal, wherein the inextensible mesh layers or fibers are configured to direct inflated motion.

Statement 23 The method of one of Statements 12-22, wherein the compressing includes one or more of molding, vacuum bags, vacuum bags with positive outside pressure, or pulling vacuum on an inside of the elastomeric foam.

Statement 24. The method of one of Statements 12-23, wherein the compressing includes one or more of vacuum, external pressure, molding, or mechanical pressure.

Statement 25. A cardiac compression device comprising a foam actuator that has a contour configured to fit over at least part of an exterior contour of a heart. The foam actuator includes an elastomeric foam, a coating disposed on the elastomeric foam, and an elastomer seal disposed on the coating. The elastomeric foam is a pre-compressed porous material. The coating is configured to constrain the elastomeric foam and is configured to break or fracture when the elastomeric foam inflates. The elastomer seal is configured to be impermeable to actuating fluid. In an example, the foam actuator in the cardiac compression device is one of the embodiments of the actuators in any one of Statements 1-10.

Statement 26. The cardiac compression device of Statement 25, wherein the device comprises a plurality of foam actuators formed in discrete regions in a continuous layer of the cardiac compression device.

Statement 27. The cardiac compression device of Statement 25 or Statement 26, wherein the cardiac compression device comprises a plurality of discrete foam actuators.

Statement 28. The cardiac compression device of Statement 27, wherein the foam actuator comprises a material that connects two or more discrete form actuators.

Statement 29. The cardiac compression device of one of Statements 25-28, wherein the foam actuator comprises a foam material that is pre-compressed.

Statement 30. The cardiac compression device of one of Statements 25-29, wherein the foam actuator comprises a foam material that has 50% to 90% porosity.

Statement 31. The cardiac compression device of one of Statements 25-30, wherein the foam actuator comprises a foam material that has a thickness of 5 mm to 50 mm.

DESCRIPTION OF THE DRAWINGS

For a fuller understanding of the nature and objects of the disclosure, reference should be made to the following detailed description taken in conjunction with the accompanying drawings.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

This disclosure describes structures that improve the efficiency of foam-based pneumatic actuators by forming the foam(s) in a state of mechanical compression prior to actuation. The disclosure also provides methods of forming foam(s) of foam-based pneumatic actuators in a state of mechanical compression prior to actuation. Embodiments of the structures disclosed herein have increased actuation deformation for a given inflation pressure; increased actuation exerted force for a given inflation pressure; control of density without changing base material components; and can provide large deformation from materials having low ultimate strains.

Figure 2:
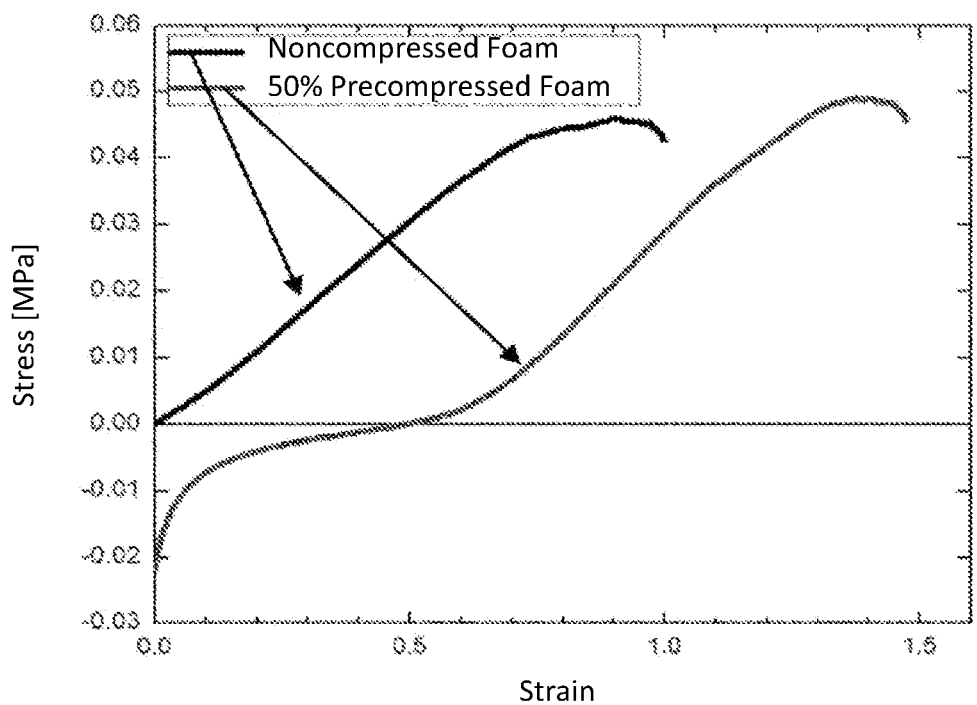
FIG. 2 illustrates tensile test of an unmodified foam and a foam that was placed in $\varepsilon=-0.5$ compression prior to testing.

Structures that increase and methods for increasing the ultimate strain of foam-based pneumatic actuators are disclosed herein. A higher ultimate strain will result in a larger potential deformation during actuation. As shown in the tensile test in FIG. 2, one way to increase the apparent ultimate strain is to place the foam in a state of compression prior to applying tension. From FIG. 2, the increase in apparent ultimate strain can be approximately equal to the amount of pre-compression applied.

Figure 1:
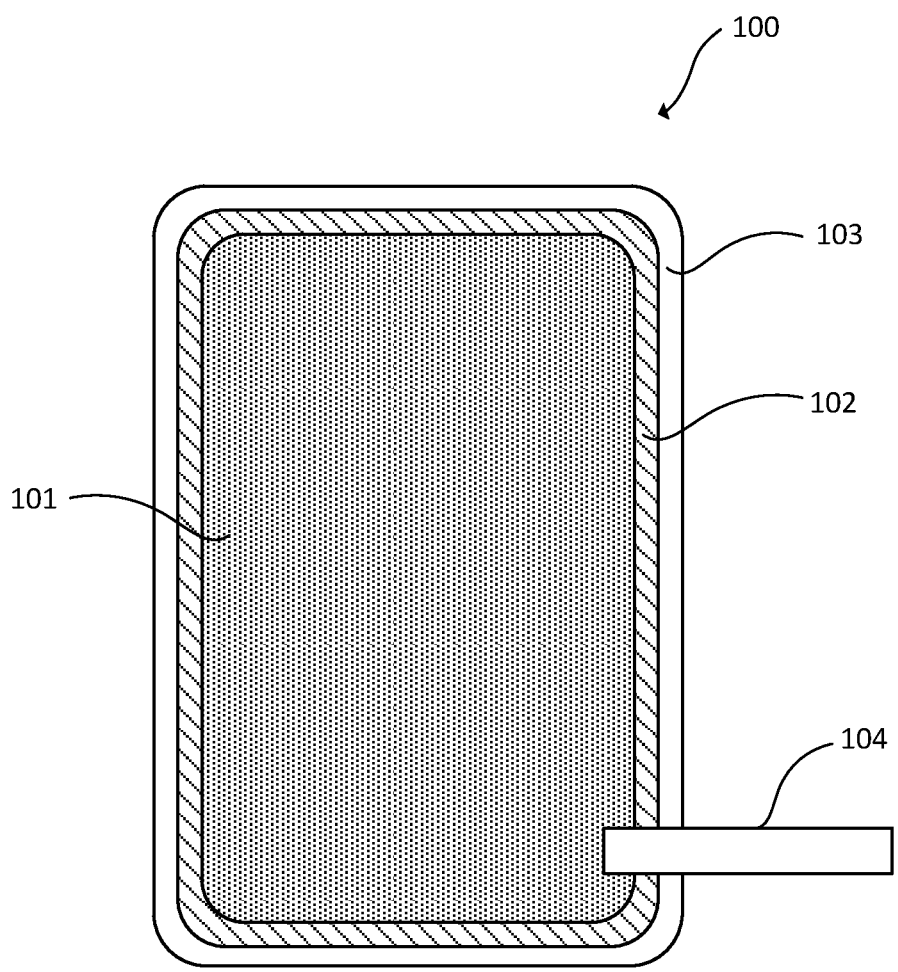
FIG. 1 is a block diagram of an embodiment of an actuator in accordance with the present disclosure.

FIG. 1 is a block diagram of an embodiment of an actuator 100. The actuator 100 includes elastomeric foam 101, a coating 102, an elastomer seal 103, and a fluid connection 104 that is connected to a fluid source (not shown). The fluid source can contain actuating fluid (e.g., air).

In an embodiment, the actuator 100 includes elastomeric foam 101, such as polyurethane (PU). The elastomeric foam can be sealed, such as to be airtight or otherwise impermeable to actuating fluid. The elastomeric foam 101 may be sealed with a non-porous polyurethane elastomer, though any compressible porous material can be used.

Figure 3:
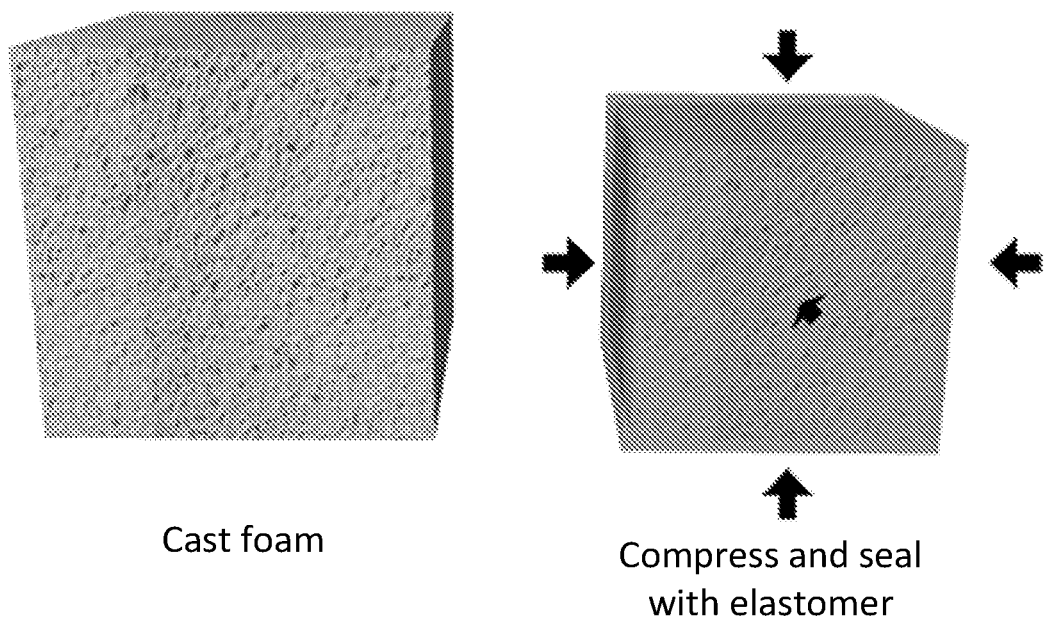
FIG. 3 is a schematic of a foam (left) triaxially compressed (right) and sealed with a thin PU elastomer coating (external layer).
Figure 4:
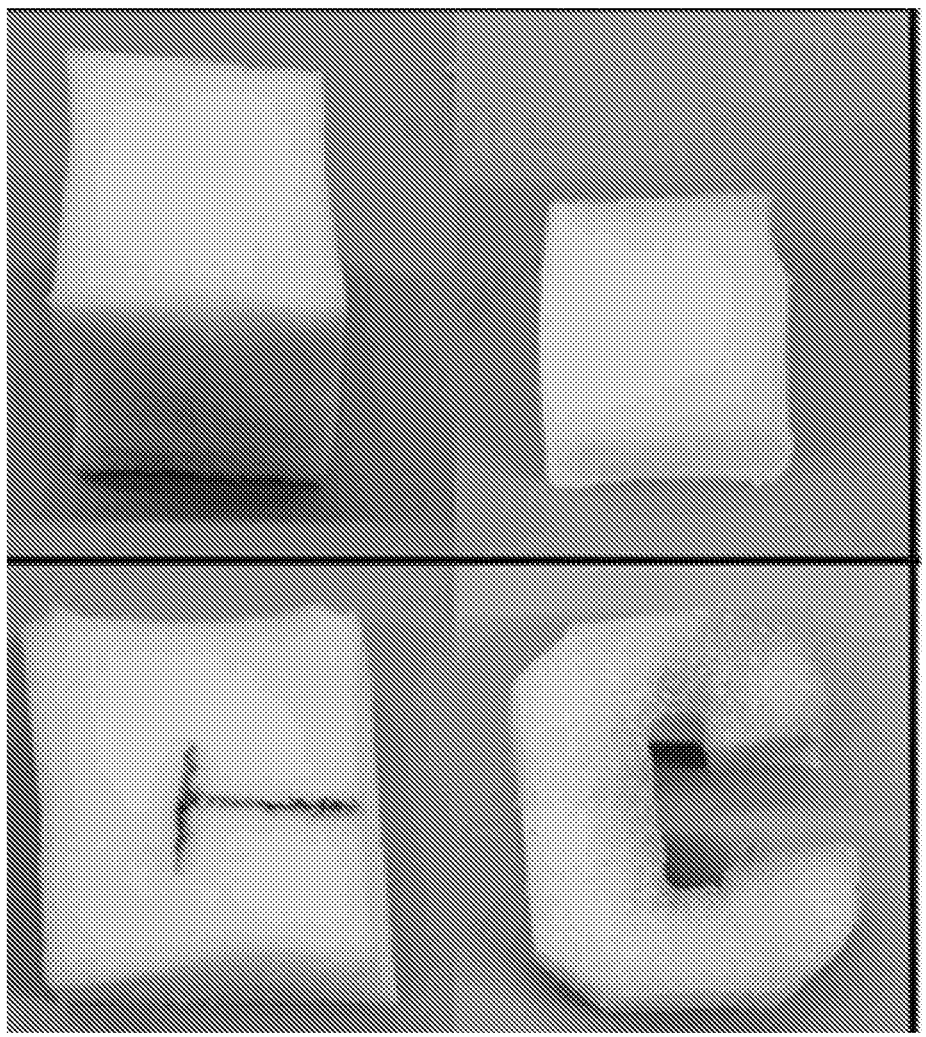
FIG. 4 shows examples of foams before (left) and after (right) being constrained by a thin PU elastomer seal. These examples show triaxial (top) and non-homogenous compression (bottom). Under triaxial compression the foam is constrained to 40% its unconstrained volume. The foam can be compressed to its densification limit which is the limit where all pores have collapsed. For highly porous foams, compression to 10% of the original foam volume may be possible.
Figure 5:
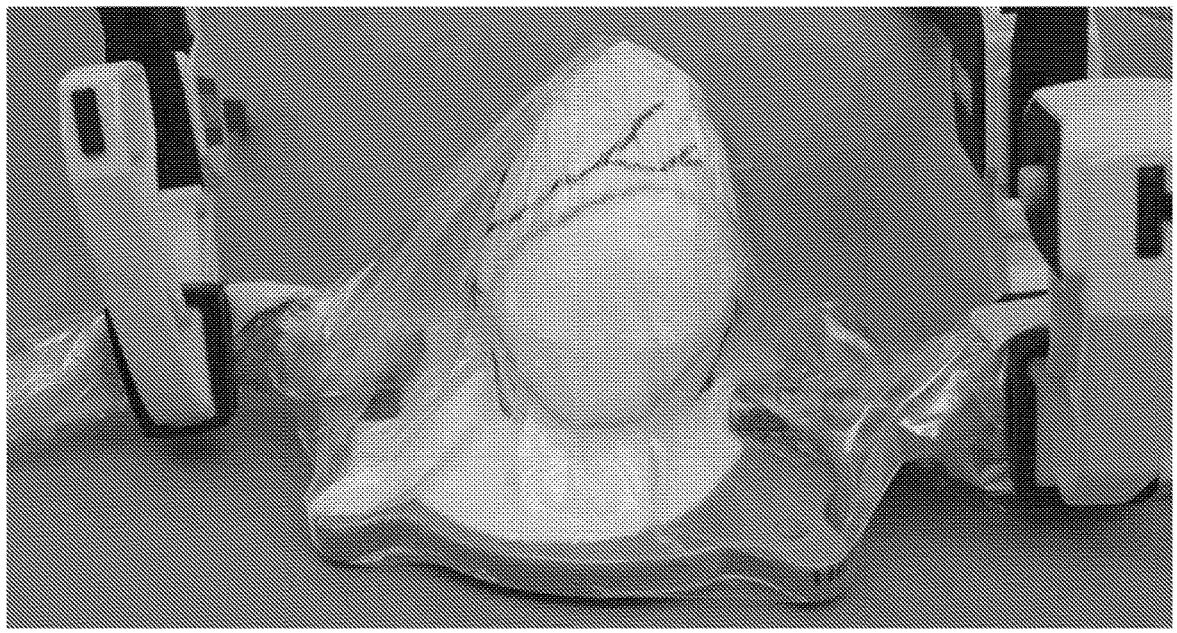
FIG. 5 illustrates hydrostatic compression of the foam by pulling vacuum within an impermeable bag.

Once the elastomeric foam 101 is formed, it is compressed and a coating 102 (e.g., ~0.5 mm) of, for example, non-porous polyurethane is applied (shown schematically in FIG. 3). This coating 102 may not be sufficiently thick to be airtight or otherwise impermeable to actuating fluid, but constrains the elastomeric foam 101 in a compressed state. In examples, constraining the elastomeric foam 101 in uniaxial, triaxial (FIG. 4 top), non-homogeneous (FIG. 4 bottom), and/or hydrostatic (FIG. 5) compression is demonstrated. Actuation beyond the original shape is possible, as shown in FIG. 5.

While the coating 102 cures, the elastomeric foam 101 is held in the compressive state using, for example, a mold or an impermeable bag with applied positive or negative pressure. Using the impermeable bag to surround the foam shape, an external positive pressure or an internal vacuum is used to compress the elastomeric foam 101 hydrostatically. Molding, vacuum bags, vacuum bags with positive outside pressure, or pulling vacuum on the inside of the elastomeric foam 101 are all examples of techniques that can be used to constrain the elastomeric foam 101. Thus, a combination of vacuum, external pressure, molding, or mechanical pressure may be used to constrain the elastomeric foam 101.

The elastomeric foam 101 can be, for example, polyurethane, silicone, styrene, butadiene rubber, latex rubber, copolymers thereof, or another porous material (e.g., an elastomer) that can be compressed and inflated. The elastomeric foam 101 also can include more than one material. The elastomeric foam 101 can have dimensions of, for example, 5 mm or larger, though other dimensions are possible. The porosity of the elastomeric foam 101 can be from 50% to 98%, including all values to the 1% and ranges between.

The elastomeric foam 101 may be compressed to approximately two-thirds of its original length, though other values are possible. The limit of compression may be the densification limit, where the foam can no longer be compressed easily. The densification limit may be dependent on the foam porosity and/or other factors.

The coating 102 can be an elastomer or another material. The coating 102 can be, for example, non-porous polyurethane, silicone, styrene, latex rubber, butadiene rubber, a thermoplastic, a thermoset polymer, a resin, or another material. The coating 102 can be the same material as the elastomeric foam 101 or a different material than the elastomeric foam 101. A bond or adhesion may form between the coating and the elastomeric foam. The coating 102 and the elastomeric foam 101 may have a difference in porosity. This difference in porosity between the coating 102 and the elastomeric foam 101 can be present whether the coating 102 and the elastomeric foam 101 are the same material or are different materials. This difference in porosity can enable the elastomeric foam 101 to be compressed and the coating 102 to constrain the compression. The elastic modulus (e.g., stiffness) and thickness dimension of the coating 102 may be configured to constrain the compressed elastomeric foam 101. The coating 102 may be sufficiently stiff (relative to the elastomeric foam 101) and applied in a thick enough layer to constrain the compression of the elastomeric foam 101.

The thickness of the coating 102 may depend on the properties of the elastomeric foam 101. The coating 102 may have a thickness from 0.5 mm to 2.0 mm, including all values to the 0.1 mm and ranges between. Larger and smaller thickness values are possible for the coating 102. The thickness of the coating 102 may be configured to be thick enough to constrain the elastomeric foam 101. The thickness of the coating 102 also may be configured to be thin enough such that motion of the actuator is not impeded during inflation. The thickness of the coating 102 may depend on the elasticity (e.g., stiffness) of the material and the stiffness (in compression) of the elastomeric foam 101.

The coating 102 can be configured to break or fracture when the elastomeric foam 101 inflates. Thus, the coating 102 can be sacrificial and can be designed to hold the elastomeric foam 101 in compression until an additional layer or coating is applied to the coating 102, such as to form a layer impermeable to the actuating fluid.

In an instance, the strain-limiting portion or portions of the coating 102 cause preferential expansion of the elastomeric foam in one or more directions and/or cause asymmetric expansion of the elastomer. By prescribing sections of the coating 102 to break upon inflation (e.g., by laser cutting perforations), the coating 102 can break apart after sealing and still provide asymmetric actuation.

The coating 102 provides a temporary constraint that allows an additional thicker elastomer seal 103 (e.g., approximately 2 mm) to be painted or molded onto the compressed foam. This thicker elastomer seal 103 may be impermeable to the actuating fluid and once applied can complete the pneumatic actuator fabrication, though inextensible mesh layers or fibers can be added to the elastomer seal 103 to further direct inflated motion. The resulting actuator 100 includes an elastomeric foam 101 in compression that is sealed with an elastomer seal 103 under zero strain.

The elastomer seal 103 can be an elastomer or another material. The elastomer seal 103 can be, for example, non-porous polyurethane, silicone, styrene, latex rubber, butadiene rubber, a thermoplastic, a thermoset polymer, a resin, or another material. The elastomer seal 103 can be the same material as the elastomeric foam 101 and/or coating 102. The elastomer seal 103 also can be a different material than the elastomeric foam 101 and/or coating 102. In contrast to the elastomeric foam 101 or coating 102, the elastomer seal 103 is configured to be impermeable to the actuating fluid (e.g., airtight). The elastomer seal 103 also can be sufficiently compliant to stretch without breaking during actuation.

The elastomer seal 103 can be configured to be impermeable to the actuating fluid. Depending on the material used for the elastomer seal 103, the thickness of the elastomer seal 103 may be >1 mm or even >2 mm. The thickness of the elastomer seal 103 may be 2× or more than 2× the thickness of the coating 102. In an example, the elastomer seal 103 is from 1 cm to 2 cm thick, which may be 100× thicker than the coating 102. The thickness of the elastomer seal 103 may be larger or smaller provided the elastomer seal 103 is impermeable to the actuating fluid.

While the coating 102 may be configured to break or fracture during actuation, the elastomer seal 103 is not. The elastomer seal 103 can be impermeable to the actuating fluid and sufficiently compliant to stretch without breaking during actuation.

Portions of the coating 102 and/or elastomer seal 103 can be applied or configured to be strain limiting by the addition of reinforcement using fibers (e.g., carbon fibers, glass fiber, or inextensible polymer mesh). For example, the coating 102 and/or elastomer seal 103 can include carbon fibers. These reinforced portions can direct the motion of the actuator 100 upon inflation. Motion can be dictated by the differential strain of different regions of the elastomer/fiber composite. In an instance, one or more layers of polymer mesh are added to the elastomer seal 103. In another instance, from 0.1% to 10% weight carbon or glass fiber is added to the elastomer seal 103. The fibers may be manually painted, adhered, or wrapped in place to direct motion during actuation.

Figure 6:
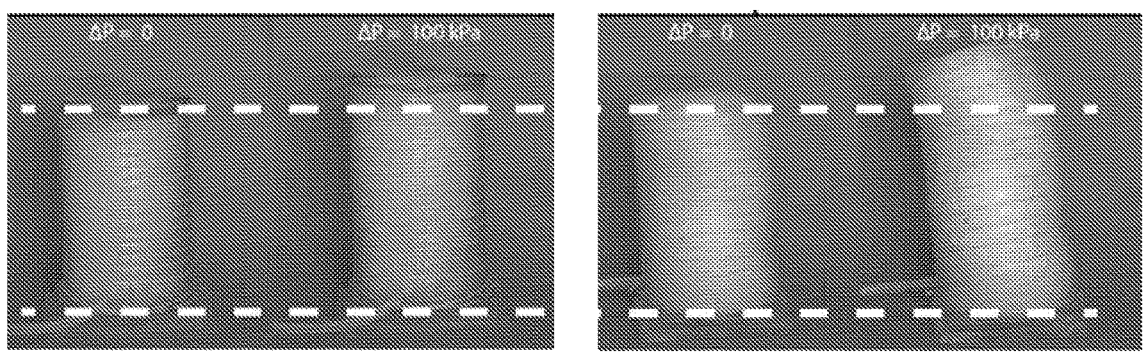
FIG. 6 illustrates actuated extension of an unmodified actuator (left) and a $\varepsilon=-0.5$ compressed foam actuator (right).
Figure 7:
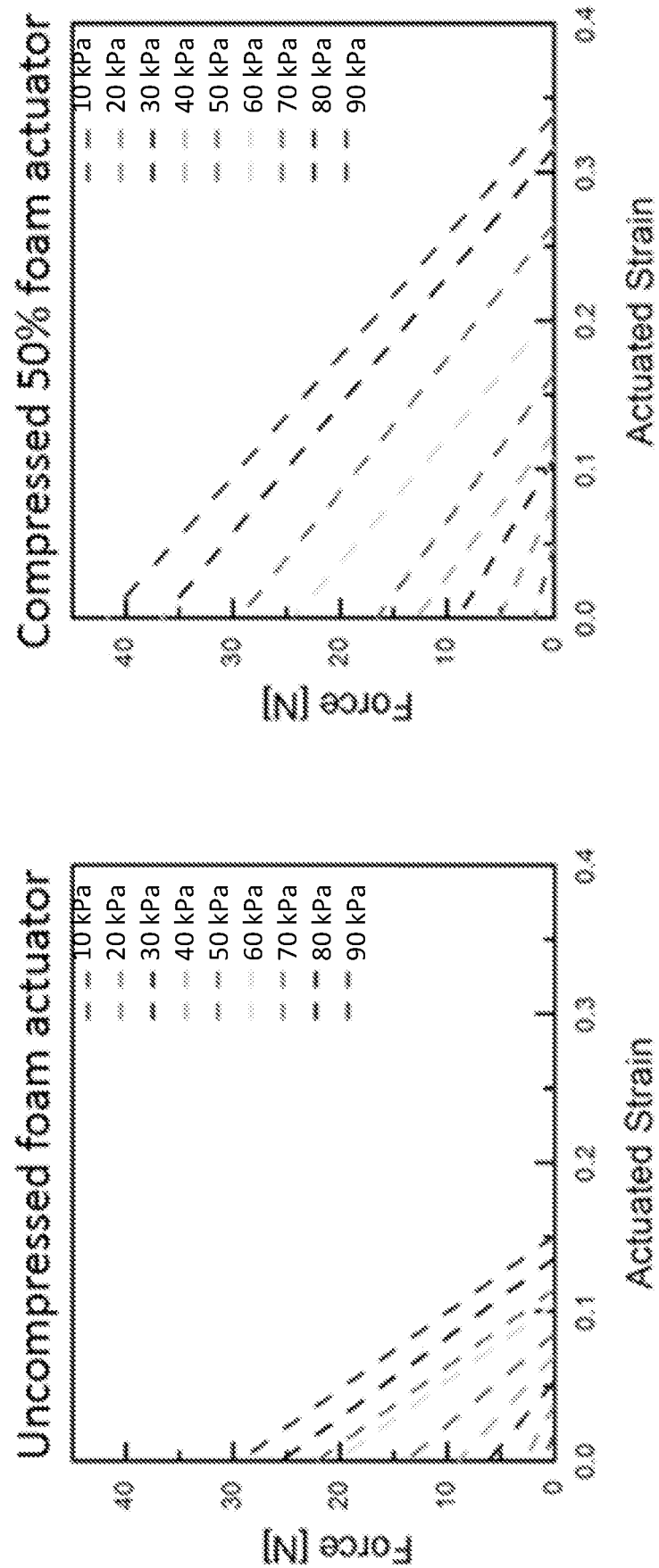
FIG. 7 shows blocked force measurements for an unmodified (left) and a $\varepsilon=-0.5$ compressed foam extending actuator (right). In both charts, the lines start at 10 kPa closest to the x-y intersect and radiate outward consecutively to 90 kPa farthest from the x-y intersect.

The elastomeric foam in the disclosed actuator can act as a compressed spring that aids in actuation upon inflation. In FIG. 6, an actuator with pre-compressed foam extends more at the same pressure than an actuator composed of unmodified foam. This behavior is further expanded in the blocked force measurements shown in FIG. 7. This test measures an actuator's maximum extending strain (with zero applied force) and maximum applied force (when constrained to zero deformation) at a range of inflation pressures. For each pressure in the tested range (10-90 kPa), the pre-compressed actuator exerts both a higher maximum force and a higher maximum strain. From this data, pre-compressed foam actuators can be viewed as either more forceful or capable of larger deformations at a given pressure or capable of more efficient actuation for a given force or deformation by requiring a lower inflation pressure. Stresses are present in the compressed foam which act to recover the foam to its non-deformed shape. These stresses aid in actuation providing higher maximum forces and strains at a given inflation pressure than uncompressed foams. In this way, the actuator may be more efficient. Pre-compressed foams can require less pressure to attain the same applied force or strain.

The elastomeric foam can be configured to expand into a larger volume than its compressed state or relaxed state. Thus, the elastomeric foam can expand beyond its compressed or relaxed state. The exampled volume of the elastomeric foam may only be limited by the maximum elongation of the materials. For example, the foam ultimate elongation may be a limiting factor.

The elastomeric foam can be configured to expand into a programmed shape, such as by using the elastomer seal. The programmed shape is a form, often different from the relaxed state shape, which may be directly dictated by the controlled strain of the actuator. By placing reinforcement layers to limit strain, the shape that the actuator will form when it is inflated can be controlled.

The elastomeric foam can be a three-dimensional shape. Thus, the resulting actuator can be curved, straight, or other shapes. The dimensions of the elastomeric foam can vary depending on the application.

Memory foam, either elastomeric or polymeric, can be used. It is sealed with the coating and then relaxed back to its original shape.

In another embodiment, the coating is avoided. The elastomeric foam is coated with the elastomer seal while in a compressed state.

The structures and methods described herein have a variety of uses. For example, they can be used in energy-efficient actuators; actuators having an increased factor of safety prior to failure; or variable density structures. In an instance, the structure and method described herein are used to fabricate a cardiac compression device.

A cardiac compression device using the elastomeric foam described herein may be an implantable, direct cardiac compression (DCC) device that surrounds the heart and applies compression on the external ventricular walls to aid in blood flow. The device can be referred to as a ventricular assist device (VAD). Porous materials, for example, porous elastomer foam, can be used to form inflation chambers that apply compression to the heart. The use of elastomer foams also allows fabrication of patient-specific devices, copying the geometry of the patient's heart through the use of standard computed tomography (CT) or magnetic resonance imaging (MRI) scanning techniques.

The devices of this disclosure use one or more foam actuators (e.g., elastomeric foam actuator) to apply cardiac compression to assist blood flow. The use of foam actuation allows more precise control over both material and mechanical design enabling the following features.

First, the device can exert localized compression on the heart avoiding potentially harmful compression of the coronary arteries and atria. For example, the actuator's size and/or position can enable localized compression.

Second, the device can be nearly entirely composed of low modulus (<1 MPa) materials (e.g., porous elastomeric materials) that can easily compress to a small form factor for less invasive implantation. This can be an advantage compared to devices composed of rigid plastic or metal that cannot easily deform.

Third, each device can be patient specific which ensures a unique custom fit. Because a device can be patient specific, there exists the possibility of physician-directed shape modification of the digital model before fabrication. This may promote reverse remodeling of the heart or inhibit ventricular aneurysms.

The cardiac compression device can include one or more foam actuators. The foam actuators can be formed from any porous material (e.g., open-cell, elastomeric foams) that can be compressed and inflated (e.g., pneumatically actuated). Any porous material that has 100% or more strain can be used. The foam actuators can comprise porous, elastomeric materials (e.g., porous elastomers). Examples of suitable porous, elastomeric materials include silicones and polyurethanes.

The foam material of the foam actuators can have a variety of porosity and/or pore size. For example, the foam material can have 50 to 90% porosity, including all integer % porosity values and ranges between. For example, the pores of the foam material can have a size (e.g., longest dimension such as, for example, a diameter for a spherical pore) of 10 microns to 1 cm, including all integer micron values and ranges between). For example, the pores of the foam material can have a size 10 to 500 microns or 10 microns to 1 mm. The pores of the foam material of an individual active area or discrete actuator can be the same or different than those of other individual active area or discrete actuator(s), respectively, of a device.

The foam material can have a variety of thickness. For example, the foam material has a thickness of 5 mm to 50 mm, including all integer mm values and ranges between. For example, the foam material has a thickness of 10 to 15 mm. The foam material can have uniform thickness or the thickness of the material can vary over a continuous layer or over individual, discrete actuators. It may be desirable to have actuators (e.g., individual active regions or discrete actuators) with different thicknesses to provide different compressive force to different regions of an individual's heart.

In an instance, the DCC device is approximately cup-shaped. It can form a shell around the lower heart that fits below the atria. Approximately two-thirds of the heart may be covered. In testing, a thread harness was used to hold the DCC device in place. The DCC device could also be held in place by suction, adhesion, and/or friction.

The cardiac compression device can include a foam-actuator layer having one or more active regions (the individual active regions can act as individual foam actuators). The foam actuator layer can be a continuous layer. The continuous layer can comprise one or more active regions (e.g., porous areas that can be actuated) and, optionally, one or more passive areas that physically connect two or more active areas. In an instance, each region can be fluidically isolated from the other regions using a second material as a barrier between the regions.

The device can comprise one or more discrete foam actuators. The discrete actuators can be physically connected by a passive material. The passive layer can be a non-porous elastomeric material. Examples of suitable elastomeric materials include silicones, polyurethanes, styrene-butadiene rubbers, and copolymers thereof. The passive layer can be a mesh or fabric (e.g. flexible polymer mesh or Kevlar fabric). The passive layer can be a shape memory material (e.g., a shape memory polyurethane foam or a shape memory alloy such as Nitinol wire).

Some or all of the discrete actuators can be interconnected. The actuator(s) can be connected to an external air source. The connection can be one or more individual lines (e.g., a pressure line and vacuum line). For example, the actuator(s) can be connected by lines having a thickness of 0.5 mm to 1 cm, including all mm values to the 0.1 and ranges between.

The foam actuator(s) can comprise a sealing layer. The foam actuator(s) can be sealed with non-porous material that provides an airtight seal or a seal that is otherwise impermeable to actuating fluid of the foam material so that it can be actuated (e.g. inflated and deflated). The sealing layer is disposed on at least a portion of or all of an exterior surface of the foam actuator or at least a portion of or all of an exterior surface of one or more discrete foam actuator. The sealing layer can be flexible and/or extensible. The sealing layer can direct the force of the foam material of the foam actuator. The sealing layer can be rigid or non-rigid. The sealing layer can be a non-porous elastomeric material. Examples of suitable elastomeric materials include silicones and polyurethanes.

All of or portions of the sealing layer can be a composite material. For example, sealing layer can be reinforced (e.g., stiffened) by addition of fibers (e.g., carbon fibers). For example, the sealing layer is a layer comprising carbon fibers. These reinforced portions can serve to direct the motion of the actuator upon inflation.

In an example, one or more of the foam actuators of the device are pre-compressed. An actuator can comprise an elastomeric foam; a coating disposed on the elastomeric foam, wherein the coating is configured to constrain the elastomeric foam and is configured to break or fracture when the elastomeric foam inflates; and an elastomer seal disposed on the coating, wherein the elastomer seal is configured to be impermeable to the actuating fluid (e.g., airtight).

The cardiac compression device surrounds at least a portion or all of the heart of an individual in which the device is implanted. The device can apply compression to at least a portion of or all of the heart (e.g., on the external ventricular walls of the heart) to aid in blood flow. The device can apply compression to different portions of the heart at the same time or a different times. In ex vivo testing, a thread harness was implemented to hold the device in contact with the heart. The thread wrapped around the top of the heart.

The cardiac compression device can be conformal (i.e., conform to the shape of an individual's heart). For example, the device can be patient specific, such as to have one or more structural features specific to an individual's heart. The device (e.g., a patient-specific device) can be made using imaging data from an individual. For example, a CT or MRI scan of the individual's (e.g., patient's) chest is taken, a 3D model of the individual's heart is made using the imaging data, and a mold is made using the 3D model (e.g., using 3D printing). The cardiac compression device can be made by forming the actuator(s) on the mold.

Figure 8:
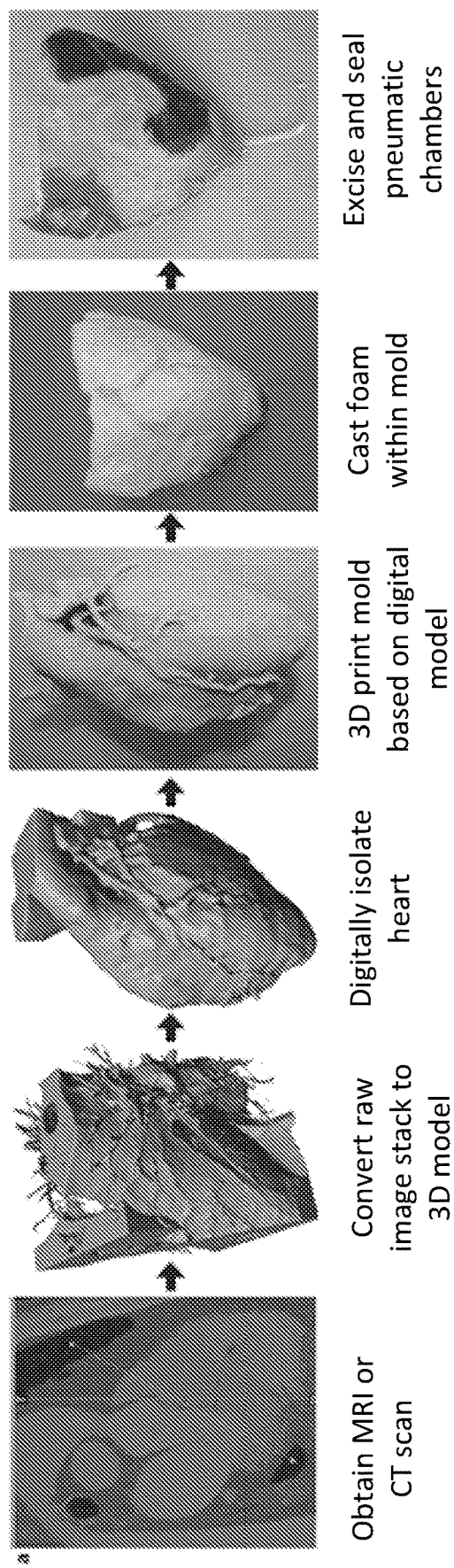
FIG. 8 illustrates a process of fabricating the patient-specific DCC device.
Figure 9:
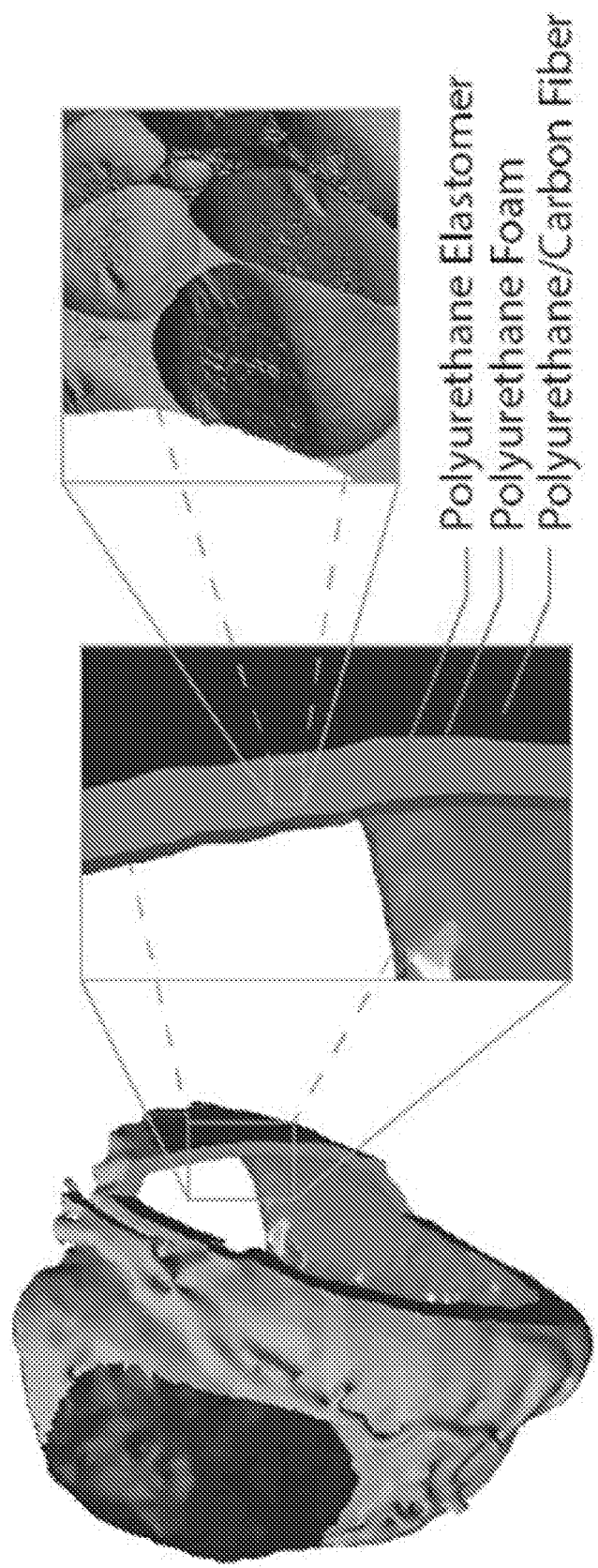
FIG. 9 illustrates a schematic of the DCC device composition.
Figure 10:
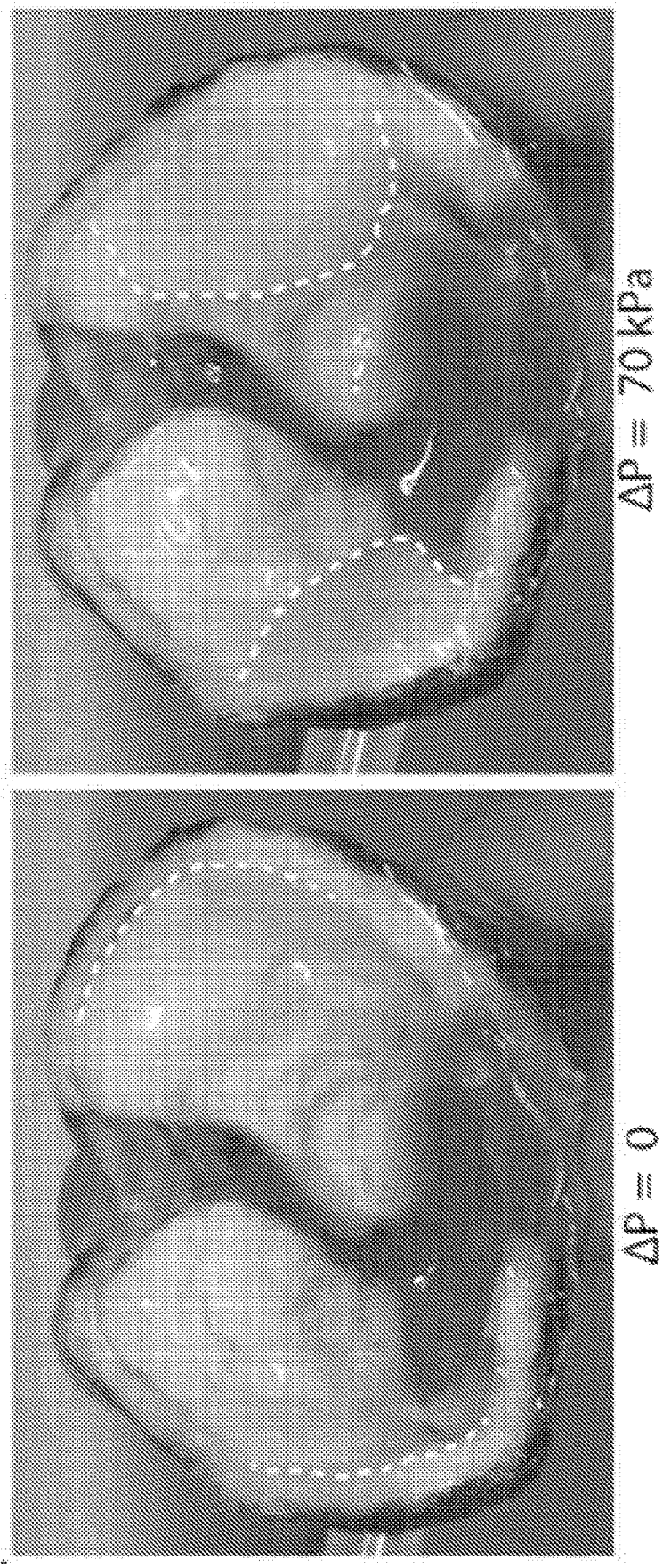
FIG. 10 illustrates inflation of the foam chambers.

The following is an example of fabrication of a cardiac compression device. DCC device fabrication (steps shown in FIG. 8) begins by collecting a standard CT or MRI scan of the patient's chest. A 3D model of the heart is digitally isolated from the scanned volume. Using this model, a mold is designed from the heart that is subsequently 3D printed. With the physical mold, a self-foaming material is cast while also identifying the locations of the coronary arteries and atria. Once the foam has solidified, the regions of the foam between coronary arteries is excised. By sealing these excised pieces in an impermeable elastomer, the pneumatic chambers that will compress each ventricle are formed. To complete the pneumatic chambers, a thin coat of PU elastomer with chopped carbon fibers is applied on the outward facing surface of the chambers. This creates a strain-limiting surface that will direct the chamber's deformation upon inflation toward the heart. The pneumatic chambers are then bound together by an elastomer, elastomer foam, extensible mesh, or any other passive, biodurable material. The resulting device is a thin shell in the shape of the patient's heart containing two inflatable foam chambers (one located on each ventricle, FIG. 9). Upon inflation (FIG. 10), these chambers compress the ventricle walls increasing blood ejection.

The device can be implanted in an individual. The individual can be a human or non-human mammal (e.g., a cat, dog, cow, or horse). It is desirable that the device not compress the coronary arteries of the individual in which the device is implanted because this restricts blood flow in an undesirable manner. The device can provide compression to all of or to a desired portion of an individual's heart. The device can be used to treat heart-related conditions, such as end-stage heart disease.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. An actuator comprising:
   an elastomeric foam, wherein the elastomeric foam is a pre-compressed porous material;
   a coating disposed on the elastomeric foam, wherein the coating is configured to constrain the elastomeric foam and is configured to break or fracture when the elastomeric foam inflates; and
   an elastomer seal disposed on the coating, wherein the elastomer seal is configured to be impermeable to actuating fluid, and wherein the pre-compressed porous material is compressed to 10% to 40% of its unconstrained volume.

2. The actuator of claim 1, wherein the porous material is one of polyurethane, silicone, styrene, latex rubber, butadiene rubber, or copolymers thereof.

3. The actuator of claim 1, wherein the coating is one of non-porous polyurethane, silicone, styrene, latex rubber, butadiene rubber, a thermoplastic, a thermoset polymer, or a resin.

4. The actuator of claim 1, wherein the elastomer seal is one of non-porous polyurethane, silicone, styrene, latex rubber, butadiene rubber, a thermoplastic, a thermoset polymer, or a resin.

5. The actuator of claim 1, wherein the coating has a thickness from 0.5 mm to 2.0 mm.

6. The actuator of claim 1, wherein the elastomer seal has a thickness of greater than or equal to 1 mm.

7. The actuator of claim 6, wherein the elastomer seal has a thickness of greater than or equal to 2 mm.

8. The actuator of claim 1, wherein the elastomer seal has a thickness at least twice a thickness of the coating.

9. The actuator of claim 1, wherein the elastomer seal is from 1 cm to 2 cm thick, and wherein the thickness of the elastomer seal is 100× thicker than a thickness of the coating.

10. The actuator of claim 1, further comprising inextensible mesh layers or fibers disposed on the elastomer seal, wherein the inextensible mesh layers or fibers are configured to direct inflated motion.

11. The actuator of claim 1, wherein the coating is configured to break and cause preferential expansion of the elastomer in one or more directions and/or cause asymmetric expansion of the elastomer.

12. A method of making an actuator according to claim 1, the method comprising:
   applying a coating to an elastomeric foam, wherein the elastomeric foam is a pre-compressed porous material compressed to 10% to 40% of its unconstrained volume, and wherein the coating is configured to constrain the elastomeric foam and is configured to break or fracture when the elastomeric foam inflates;
   compressing the elastomeric foam after applying the coating; and
   applying an elastomer seal to the coating, wherein the elastomer seal is configured to be impermeable to actuating fluid.

13. The method of claim 12, wherein the method is configured to form the foam in a state of mechanical compression prior to actuation.

14. The method of claim 12, wherein the elastomeric foam is one of polyurethane, silicone, styrene, latex rubber, butadiene rubber, copolymers thereof, or another porous material.

15. The method of claim 12, wherein the coating is one of non-porous polyurethane, silicone, styrene, latex rubber, butadiene rubber, a thermoplastic, a thermoset polymer, or a resin.

16. The method of claim 12, wherein the elastomer seal is one of non-porous polyurethane, silicone, styrene, latex rubber, butadiene rubber, a thermoplastic, a thermoset polymer, or a resin.

17. The method of claim 12, wherein the coating has a thickness from 0.5 mm to 2.0 mm.

18. The method of claim 12, wherein the elastomer seal has a thickness of greater than or equal to 1 mm.

19. The method of claim 18, wherein the elastomer seal has a thickness of greater than or equal to 2 mm.

20. The method of claim 12, wherein the elastomer seal has a thickness 2× or more than 2× a thickness of the coating.

21. The method of claim 12, wherein the elastomer seal is from 1 cm to 2 cm thick, and wherein the thickness of the elastomer seal is 100× thicker than a thickness of the coating.

22. The method of claim 12, further comprising applying inextensible mesh layers or fibers to the elastomer seal, wherein the inextensible mesh layers or fibers are configured to direct inflated motion.

23. The method of claim 12, wherein the compressing includes one or more of molding, vacuum bags, vacuum bags with positive outside pressure, or pulling vacuum on an inside of the elastomeric foam.

24. The method of claim 12, wherein the compressing includes one or more of vacuum, external pressure, molding, or mechanical pressure.

25. A cardiac compression device comprising:
   an actuator of claim 1, wherein the foam actuator has a contour configured to fit over at least part of an exterior contour of a heart.

26. The cardiac compression device of claim 25, wherein the device comprises a plurality of foam actuators formed in discrete regions in a continuous layer of the cardiac compression device.

27. The cardiac compression device of claim 25, wherein the cardiac compression device comprises a plurality of discrete foam actuators.

28. The cardiac compression device of claim 27, wherein the foam actuator comprises a material that connects two or more discrete form actuators.

29. The cardiac compression device of claim 25, wherein the foam actuator comprises a foam material that is pre-compressed.

30. The cardiac compression device of claim 25, wherein the foam actuator comprises a foam material that has 50% to 90% porosity.

31. The cardiac compression device of claim 25, wherein the foam actuator comprises a foam material that has a thickness of 5 mm to 50 mm.

32. The actuator of claim 1, wherein the elastomeric foam has a first state as a pre-compressed porous material, a second state after the coating break such that the elastomeric foam relaxes back to its original shape, and optionally a third state such that the elastomeric foam is configured to expand into a larger volume than the first state or the second state.

* * * * *